United States Patent
Zinobile (10) Patent No.: US 8,637,698 B2
(45) Date of Patent: Jan. 28, 2014

(54) PRODUCTION OF ACETIC ACID WITH AN INCREASED PRODUCTION RATE

(75) Inventor: Raymond J. Zinobile, Houston, TX (US)

(73) Assignee: Celanese International Corporation, Dallas, TX (US)

( * ) Notice: Subject to any disclaimer, the term of this patent is extended or adjusted under 35 U.S.C. 154(b) by 452 days.

(21) Appl. No.: 12/950,520

(22) Filed: Nov. 19, 2010

(65) Prior Publication Data

US 2012/0130123 A1    May 24, 2012

(51) Int. Cl.
    *C07C 51/12*    (2006.01)
(52) U.S. Cl.
    USPC ........................................................ 562/519
(58) Field of Classification Search
    None
    See application file for complete search history.

(56) References Cited

U.S. PATENT DOCUMENTS

| | | |
|---|---|---|
| 4,039,395 A | 8/1977 | Eby |
| 5,334,755 A | 8/1994 | Yoneda et al. |
| 5,364,963 A | 11/1994 | Minami et al. |
| 6,114,576 A | 9/2000 | Leet et al. |
| 7,576,236 B2 | 8/2009 | Bhaskaran et al. |
| 2009/0270650 A1 | 10/2009 | Patt |
| 2009/0299092 A1* | 12/2009 | Beavis et al. ................. 562/519 |

FOREIGN PATENT DOCUMENTS

| | | |
|---|---|---|
| EP | 0 567 331 A2 | 10/1993 |
| WO | WO 2007/071902 A1 | 6/2007 |

OTHER PUBLICATIONS

International Search Report and Written Opinion mailed Aug. 16, 2012 in corresponding International Application No. PCT/US2011/061316.

* cited by examiner

*Primary Examiner* — Yevegeny Valenrod (57) ABSTRACT

A method for producing acetic acid at increased production rates. The method may include a heat transfer system for generating a steam product from the heat of the reaction. In addition, the method may include multiple drying columns. The steam product may be integrated with at least one of the multiple drying columns.

19 Claims, 3 Drawing Sheets

PRODUCTION OF ACETIC ACID WITH AN INCREASED PRODUCTION RATE

FIELD OF THE INVENTION

The present invention is directed to a method for producing acetic acid from carbon monoxide and, in particular, to improved processes, wherein the process comprises a first and second drying column. The present invention also relates to a method of generating steam from the heat of the reaction.

BACKGROUND OF THE INVENTION

A widely used and successful commercial process for synthesizing acetic acid involves the catalyzed carbonylation of methanol with carbon monoxide. The catalysis contains rhodium and/or iridium and a halogen promoter, typically methyl iodide. The reaction is conducted by continuously bubbling carbon monoxide through a liquid reaction medium in which the catalyst is dissolved. The reaction medium also comprises methyl acetate, water, methyl iodide and the catalyst. Conventional commercial processes for carbonylation of methanol include those described in U.S. Pat. Nos. 3,769,329, 5,001,259, 5,026,908, and 5,144,068, the entire contents and disclosures of which are hereby incorporated by reference. Another conventional methanol carbonylation process includes the Cativa™ process, which is discussed in Jones, J. H. (2002), "*The Cativa™ Process for the Manufacture of Acetic Acid*," Platinum Metals Review, 44 (3): 94-105, the entire content and disclosure of which is hereby incorporated by reference.

In the production of acetic acid there may be several limits on the capacity of the system. One such limit is the removal of heat from the reaction. Methanol carbonylation is an exothermic reaction and regulating the heat is necessary for maintaining efficient production rates. Conventional systems use a flasher to remove about half of the heat of the reaction. U.S. Pat. No. 5,364,963 also describes a cooling a portion of the carbonylation product with an indirect hear exchange. As production increase the heat that needs to be remove also increases. Removing the increase in heat with the flasher may be less efficient, and may reduce the overall production of acetic acid.

The heat of the reaction may also be recovered. U.S. Pat. No. 6,175,039 discloses removing the heat of reaction from the highly exothermic process by using a steam boiler heated by the pump-around stream. The heat from the reaction may also be transferred to other systems. U.S. Pat. No. 6,114,576 discloses a process for the production of carboxylic acid in the presence of solid catalyst particles that uses the exothermic heat of reaction with high efficiency in recovering the carboxylic acid product. This process uses indirect heat exchange to transfer the heat of reaction to another stream, without the need for an additional heat transfer fluid such as steam. U.S. Pat. No. 7,465,823 discloses a process and system in which a portion of the heat produced during the production of the acetic acid is transferred to a vinyl acetate production and/or purification process and system to facilitate production and/or purification of a vinyl acetate product.

Increasing production rates may also place capacity limitations on the purification systems. Expanding capacity in commercial purification systems requires increasing the size of the distillation columns. Larger distillation columns also may require reconfiguration of the column, piping, foundations, and utilities to expand capacity. The associated downtime to increase capacity make these changeovers to larger-capacity distillation columns economically unattractive.

As will be appreciated by one of skill in the art, there is always incentive for improvement to existing processes for the production of acetic acid. The present invention provides some such improvements.

SUMMARY OF THE INVENTION

In a first embodiment, the present invention is directed to a carbonylation method of producing acetic acid comprising the steps of reacting carbon monoxide with at least one reactant in a reactor containing a reaction medium to produce a reaction product comprising acetic acid, wherein the at least one reactant is selected from the group consisting of methanol, methyl acetate, methyl formate, dimethyl ether and mixtures thereof, and wherein the reaction medium comprises water, a halogen promoter, and a catalyst; separating the reaction product in a flasher to produce a crude product stream and a liquid recycle stream; purifying the crude product stream in a light ends column to produce a purified product stream; drying a first portion of the purified product stream in a first drying column; and drying a second portion of the purified product stream in a second drying column.

In a second embodiment, the present invention is directed to a carbonylation method of producing acetic acid comprising the steps of reacting carbon monoxide with at least one reactant in a reactor containing a reaction medium to produce a reaction product comprising acetic acid, wherein the at least one reactant is selected from the group consisting of methanol, methyl acetate, methyl formate, dimethyl ether and mixtures thereof, and wherein the reaction medium comprises water, a halogen promoter, and a catalyst; separating the reaction product in a flasher to produce a crude product stream and a liquid recycle stream; purifying the crude product stream in a light ends column to produce a purified product stream; drying a first portion of the purified product stream in a first drying column; and drying a second portion of the purified product stream in a second drying column, wherein the method further comprises generating steam from heat from the reaction that produces the reaction product in a heat transfer system; and transferring at least a portion of the steam to the second drying column, wherein the steam provides a portion of the energy required to drive separation in the second drying column.

In a third embodiment, the present invention is directed to a method for controlling the reaction temperature in an acetic acid production process comprising the steps of reacting carbon monoxide with at least one reactant in a reactor containing a reaction medium to produce a reaction product comprising acetic acid, wherein the at least one reactant is selected from the group consisting of methanol, methyl acetate, methyl formate, dimethyl ether and mixtures thereof, and wherein the reaction medium comprises water, a halogen promoter, and a catalyst; separating the reaction product in a flasher to produce a crude product stream and a liquid recycle stream; distilling the crude product stream to produce an acetic acid product stream in one or more distillation columns; and generating steam from heat of the reaction that produces the reaction product in a heat transfer system.

In a fourth embodiment, the present invention is directed to a method for controlling the reaction temperature in an acetic acid production process comprising the steps of reacting carbon monoxide with at least one reactant in a reactor containing a reaction medium to produce a reaction product comprising acetic acid, wherein the at least one reactant is selected from the group consisting of methanol, methyl acetate, methyl formate, dimethyl ether and mixtures thereof, and wherein the reaction medium comprises water, a halogen promoter, and a catalyst; separating the reaction product in a flasher to produce a crude product stream and a liquid recycle stream; distilling the crude product stream to produce an acetic acid product stream in one or more distillation columns; and generating steam from heat of the reaction that produces the reaction product in a heat transfer system, wherein the method further comprises transferring a portion of the steam to the one or more distillation columns, wherein the steam provides a portion of the energy required to drive separation in the one or more distillation columns.

BRIEF DESCRIPTION OF DRAWINGS

The invention is described in detail below with reference to the appended drawings, wherein like numerals designate similar parts.

DETAILED DESCRIPTION OF THE INVENTION

The present invention generally relates to acetic acid production and increases in acetic acid production. As a result of increasing production, there may be additional heat from the reaction and more crude product to purify. In one embodiment, the present invention relates to generating steam from the carbonylation process in a heat transfer system. In another embodiment, the present invention relates to the use of multiple parallel columns to purify acetic acid withdrawn from the light ends column. In preferred embodiments, the generated steam from the acetic acid production may be transferred to at least one of the multiple parallel columns to drive the separation therein. Preferably the generated steam may be transferred to the parallel column that operates at a lower base temperature. Embodiments of the present invention provide processes for improving the efficiency at increased production rates of acetic acid. Advantageously the embodiments of the present invention may mitigate capacity limitations in the purification process.

The acetic acid produced by carbonylation of methanol or through the catalytic oxidation of ethylene and/or ethane is exothermic. Conventionally, a significant portion of the heat of reaction generated in the production of acetic acid is dissipated, thereby losing the energy produced. In one embodiment, a heat transfer system of the present invention recovers energy from acetic acid production in the form of steam. The heat transfer system may generate steam that has a pressure from 1 to 15 barg, e.g., 2 to 14 barg, or 3 to 14 barg. Preferably the steam generated by the heat transfer system is a variable quality steam having a pressure of greater than 5 barg, e.g., greater than 7 barg. Although low quality steam may also be produced, it is preferred that the heat transfer system generates variable quality steam. The generated steam may be directed in whole or part to one or more industrial chemical production units, such as vinyl acetate production, or supplied to a reboiler of one or more of the distillation columns used for purifying the acetic acid.

In one embodiment, acetic acid production may be increased by using multiple columns to purify an acetic acid side stream withdrawn of the light ends column. In particular, multiple drying columns may be used in parallel. In another embodiment, the heat of the carbonylation reactor may be regulated using a pump around loop that may produce steam. The production of steam also removes additional heat of the reaction at higher production rates. Preferably, the steam produced may supply energy required to drive separation in one or more distillation columns in the purification section. Embodiments of the present invention advantageously allow for an increased capacity of the system and the efficient transfer of energy within the production process. While not being bound to one particular theory, the present invention improves the overall production of acetic acid by increasing the capacity of the drying process in the purification section of the process and conserving the exothermic energy of the carbonylation reaction within the process.

The present invention may be applied in any methanol carbonylation process. Exemplary carbonylation systems that may be used with embodiments of the present invention include those described in U.S. Pat. Nos. 7,223,886, 7,005,541, 6,657,078, 6,339,171, 5,731,252, 5,144,068, 5,026,908, 5,001,259, and 4,994,608, and U.S. Pub. Nos. 2008/0287706, 2008/0293966, 2009/0107833, and 2009/0270651, the entire contents and disclosures of which are hereby incorporated by reference. A carbonylation system may comprise a carbonylation section and a purification section. Any suitable purification section may be used in combination with any of the embodiments of the present invention. Suitable purification sections are described in the patents referenced above and typically include a light ends column, a drying column, one or more columns for removal of permanganate reducing compounds (PRC's), guard beds, vent scrubbers, and/or heavy ends columns.

Figure 1:
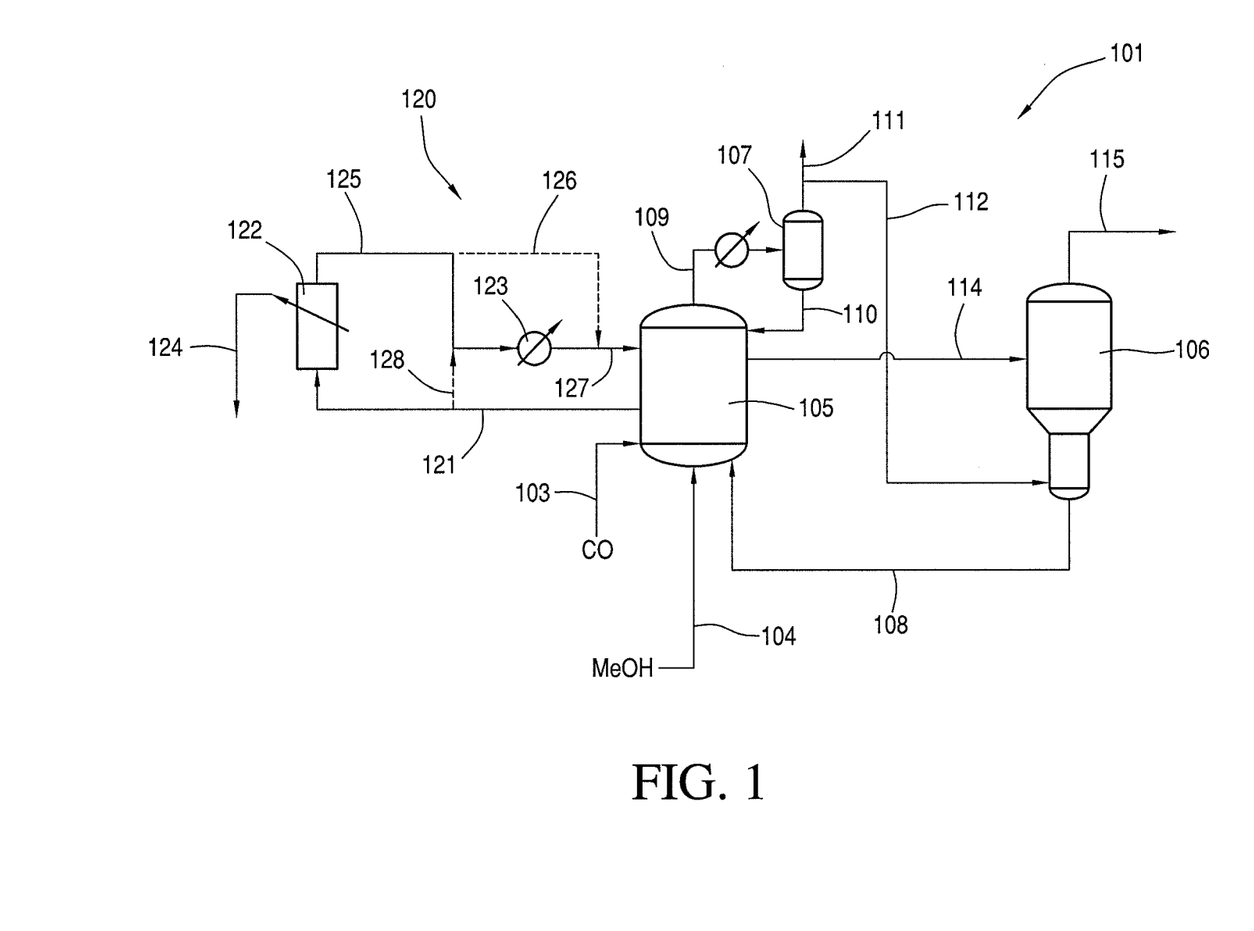
FIG. 1 illustrates a carbonylation section for generating steam from the reaction heat according to an embodiment of the present invention.

An exemplary carbonylation section 101 is shown in FIG. 1. Carbonylation section 101 comprises carbon monoxide feed stream 103, reactant feed stream 104, reactor 105, and flasher 106. Carbon monoxide and at least one reactant are fed by feed streams 103 and 104, respectively, to lower portion of reactor 105. Reactant feed stream 104 supplies at least one reactant selected from the group consisting of methanol, methyl acetate, methyl formate, dimethyl ether and/or mixtures thereof, to reactor 105. In preferred embodiments, reactant feed stream 104 supplies methanol and methyl acetate. Optionally, reactant feed stream 104 may be connected to one or more vessels (not shown) that store fresh reactants for the carbonylation process. In addition, there may be a methyl iodide storage vessel (not shown) and/or catalyst vessel (not shown) connected to reactor 105 for supplying fresh methyl iodide and catalyst as needed to maintain reaction conditions. In other embodiments, all or some of the methanol and/or reactive derivatives thereof supplied to reactor 105 may be in the form of scrubbed methanol from another location in the system or as a product or by-product of another system.

One or more recycle feed streams from carbonylation section 101 may be fed to reactor 105 via line 108. As discussed herein, recycle feed stream 108 may comprise the components of the reaction medium, as well as residual and/or entrained catalyst and acetic acid. Although one recycle feed stream 108 is shown in FIG. 1, there may be multiple streams that are fed separately to reactor 105. For example, one or more recycle feed streams from a purification section (not shown) may be fed to reactor 105 via line 108. Preferably, the recycle feed streams fed via line 108 are introduced in the lower portion of reactor 105.

In certain embodiments of the invention, reactant feed stream 104 comprises methanol and/or reactive derivatives thereof. Suitable reactive derivatives of methanol include methyl acetate, dimethyl ether, methyl formate and mixtures thereof. In one embodiment, a mixture of methanol and reactive derivatives of methanol is used as a reactant in the process of the present invention. Preferably, methanol and/or methyl acetate are used as reactants. At least some of the methanol and/or reactive derivatives thereof will be converted to, and hence be present as, methyl acetate in the liquid reaction composition by reaction with acetic acid product or solvent. The concentration of methyl acetate in the liquid reaction composition is preferably in the range from 0.5 wt. % to 70 wt. %, e.g., from 0.5 wt % to 50 wt. %, or from 1 wt. % to 35 wt. %, of the total weight of the liquid reaction composition.

Carbon monoxide feed stream 103 may be essentially pure or may contain small amounts of inerts and impurities such as carbon dioxide, methane, nitrogen, hydrogen, noble gases, water and $C_1$ to $C_4$ paraffinic hydrocarbons. The presence of hydrogen in the carbon monoxide and generated in situ by the water gas shift reaction is preferably kept low (e.g., less than 1 bar partial pressure or less than 0.5 bar partial pressure), as its presence may result in the formation of hydrogenation products. The partial pressure of carbon monoxide in the reaction in carbonylation section 101 is preferably in the range from 1 bar to 70 bar, e.g., from 1 bar to 35 bar, or from 1 bar to 15 bar.

In some embodiments of the invention, within reactor 105, methanol is reacted with carbon monoxide in a homogeneous catalytic reaction system comprising a reaction solvent, methanol and/or reactive derivatives thereof, a Group VIII catalyst, at least a finite concentration of water and optionally an iodide salt.

Suitable Group VIII catalysts include rhodium and/or iridium catalysts. When a rhodium catalyst is used, the rhodium catalyst may be added in any suitable form such that rhodium is in the catalyst solution as an equilibrium mixture including $[Rh(CO)_2I_2]^-$ anion, as is well known in the art. Preferably, the catalyst is a rhodium diiodide dicarbonyl anion that is ionically bound to a suitable resin, e.g., polyvinylpyridine. Iodide salts optionally maintained in the reaction mixtures of the processes described herein may be in the form of a soluble salt of an alkali metal or alkaline earth metal or a quaternary ammonium or phosphonium salt. In certain embodiments, the catalyst co-promoter is lithium iodide, lithium acetate, or mixtures thereof. The salt co-promoter may be added as a non-iodide salt that will generate an iodide salt. The iodide catalyst stabilizer may be introduced directly into the reaction system. Alternatively, the iodide salt may be generated in-situ since under the operating conditions of the reaction system, a wide range of non-iodide salt precursors will react with methyl iodide to generate the corresponding co-promoter iodide salt stabilizer. For additional detail regarding rhodium catalysis and iodide salt generation, see U.S. Pat. Nos. 5,001,259, 5,026,908 and 5,144,068, the entireties of which are hereby incorporated by reference.

When an iridium catalyst is used, the iridium catalyst may comprise any iridium-containing compound that is soluble in the liquid reaction composition. The iridium catalyst may be added to the liquid reaction composition for the carbonylation reaction in any suitable form that dissolves in the liquid reaction composition or is convertible to a soluble form. Examples of suitable iridium-containing compounds that may be added to the liquid reaction composition include: $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_2I_2]^-H^+$, $[Ir(CO)^-_2Br_2]^-H^+$, $[Ir(CO)_2I_4]^-H^+$, $[Ir(CH_3)I_3(CO)_2]^-H^+$, $Ir_4(CO)_{12}$, $IrCl_3 \cdot 3H_2O$, $IrBr_3 \cdot 3H_2O$, $Ir_4(CO)_{12}$, iridium metal, $Ir_2O_3$, $Ir(acac)(CO)_2$, $Ir(acac)_3$, iridium acetate, $[Ir_3O(OAc)_6(H_2O)_3][OAc]$ and hexachloroiridic acid $[H_2IrCl_6]$. Chloride-free complexes of iridium such as acetates, oxalates and acetoacetates are usually employed as starting materials. The iridium catalyst concentration in the liquid reaction composition is generally in the range of 100 to 6000 ppm. The carbonylation of methanol utilizing iridium catalyst is well known and is generally described in U.S. Pat. Nos. 5,942,460, 5,932,764, 5,883,295, 5,877,348, 5,877,347 and 5,696,284, the entireties of which are hereby incorporated by reference.

A halogen co-catalyst/promoter is generally used in combination with the Group VIII metal catalyst component. Methyl iodide is a preferred as the halogen promoter. Preferably, the concentration of halogen promoter in the liquid reaction composition is in the range 1 wt. % to 50 wt. %, and preferably 2 wt. % to 30 wt. %.

The alkyl halide promoter may be combined with a salt stabilizer/co-promoter compound, which may include salts of a metal of Group IA or Group IIA, or a quaternary ammonium or phosphonium salt. Particularly preferred are iodide or acetate salts, e.g., lithium iodide or lithium acetate.

Other promoters and co-promoters may be used as part of the catalytic system of the present invention, as described in EP0849248, the entirety of which is hereby incorporated by reference. Suitable promoters are selected from ruthenium, osmium, tungsten, rhenium, zinc, cadmium, indium, gallium, mercury, nickel, platinum, vanadium, titanium, copper, aluminum, tin, antimony, and are more preferably selected from ruthenium and osmium. Specific co-promoters are described in U.S. Pat. No. 6,627,770, the entirety of which is incorporated herein by reference.

A promoter may be present in an effective amount up to the limit of its solubility in the liquid reaction composition and/or any liquid process streams recycled to the reactor from the acetic acid recovery stage. When used, the promoter is suitably present in the liquid reaction composition at a molar ratio of promoter to metal catalyst of 0.5:1 to 15:1, preferably 2:1 to 10:1, more preferably 2:1 to 7.5:1. A suitable promoter concentration is 400 to 5000 ppm.

Water may be formed in situ in the liquid reaction composition, for example, by the esterification reaction between methanol reactant and acetic acid product. In some embodiments, water is introduced to reactor 105 together with or separately from other components of the liquid reaction composition. Water may be separated from the other components of reaction composition withdrawn from reactor 105 and may be recycled in controlled amounts to maintain the required concentration of water in the liquid reaction composition. Preferably, the concentration of water maintained in the liquid reaction composition is in the range from 0.1 wt. % to 16 wt. %, e.g., from 1 wt. % to 14 wt. %, or from 1 wt. % to 10 wt. % of the total weight of the reaction composition.

In accordance with a preferred carbonylation process of the present invention, the desired reaction rates are obtained even at low water concentrations by maintaining, in the reaction medium, an ester of the desired carboxylic acid and an alcohol, desirably the alcohol used in the carbonylation, and an additional iodide ion that is over and above the iodide ion that is present as hydrogen iodide. An example of a preferred ester is methyl acetate. The additional iodide ion is desirably an iodide salt, with lithium iodide being preferred. It has been found, as described in U.S. Pat. No. 5,001,259, that under low water concentrations, methyl acetate and lithium iodide act as rate promoters only when relatively high concentrations of each of these components are present and that the promotion is higher when both of these components are present simultaneously. The absolute concentration of iodide ion content is not a limitation on the usefulness of the present invention.

In reactor 105 the reaction medium is maintained, preferably automatically, at a predetermined level. This predetermined level may remain substantially constant during normal operation. Into reactor 105, methanol, carbon monoxide, and sufficient water may be continuously introduced as needed to maintain at least a finite concentration of water in the reaction medium. In some embodiments, carbon monoxide (e.g., in the gaseous state) is continuously introduced into reactor 105. Carbon monoxide feed 103 is introduced at a rate sufficient to maintain the desired total reactor pressure. The temperature of reactor 105 may be controlled using heat exchangers in a pump around loops, as illustrated in the embodiments shown in FIG. 1.

Acetic acid is typically manufactured in a liquid phase reaction at a temperature from about 160° C. to about 220° C. and a total pressure from about 20 bar to about 50 bar. In some embodiments of the invention, reactor 105 is operated at a temperature from 150° C. to 250° C., e.g., from 155° C. to 235° C., or from 160° C. to 220° C. Certain embodiments of the present invention are directed to methods for the synthesis of acetic acid where the carbonylation reaction temperature is performed at temperatures elevated to above about 190° C. Exemplary reaction temperatures for carbonylation are from about 190° C. to about 225° C., including about 200° C. to about 220° C. The elevated reaction temperature may facilitate lowering of the reactor catalyst concentration and increase acetic acid production rates. The pressure of the carbonylation reaction is preferably from 10 to 200 bar, more preferably 10 to 100 bar and most preferably 15 to 50 bar.

In a typical carbonylation process, carbon monoxide is continuously introduced into the carbonylation reactor, desirably below the agitator, which may be used to rouse the contents. The gaseous feed preferably is thoroughly dispersed through the reacting liquid by this roused, excited stirring means. A gaseous purge stream 109 is vented from reactor 105 to prevent buildup of gaseous by-products and to maintain a set carbon monoxide partial pressure at a given total reactor pressure. The temperature of the reactor may be controlled and the carbon monoxide feed is introduced at a rate sufficient to maintain the desired total reactor pressure. Gaseous purge stream 109 may be scrubbed with acetic acid and/or methanol in recovery unit 107 to recover low boiling components. The gaseous purge stream 109 may be partially condensed and the non-condensable portion is fed to a recovery unit 107 which may return low boiling components to the top of reactor 105 via stream 110. The condensable components 110 may comprise methyl acetate, water, and/or methyl iodide. Carbon monoxide in the gaseous purge stream may be purged in line 111 or fed via line 112 to base of flasher 106 to enhance rhodium stability.

Carbonylation product is drawn off from carbonylation reactor 105 at a rate sufficient to maintain a constant level therein and is provided to a flasher 106 via stream 114. In flasher 106, the carbonylation product is separated in a flash separation step with or without the addition of heat to obtain a crude product stream 115 comprising acetic acid, and a liquid recycle stream, comprising a catalyst-containing solution, that is preferably recycled to the reactor via stream 108. The catalyst-containing solution predominantly contains acetic acid, the rhodium catalyst, and the iodide salt, along with lesser quantities of methyl acetate, methyl iodide, and water, as discussed above. The crude product stream 115 comprises acetic acid, methyl iodide, methyl acetate, water, alkanes and PRC's. The crude product stream 115 from flasher 106 is directed to a purification section.

Referring to FIG. 1, a reaction section 101 of the present invention may further comprise a heat transfer system 120. A reactor solution stream 121 may be taken directly from reactor 105 as shown in FIG. 1 or optionally may be withdrawn from the carbonylation product stream 114 via a pump around loop (not shown). In operation, reactor solution stream 121 may be withdrawn at a temperature that is substantially similar to the reaction temperature and may be at a temperature from 150° C. to 250° C. Heat transfer system 120 may comprise one or more steam generator 122 and/or heat exchanger 123. For purposes of clarity one steam generator 122 and heat exchanger 123 as shown in FIG. 1. Additional steam generators and/or heat exchanges may be used in embodiments of the present invention. Heat transfer system 120 may also comprise pumps, variable speed electric motors and/or steam turbines, valves and controls for regulating the flow of the reaction solution stream 121 through heat transfer system 120.

In one embodiment, reactor solution stream 121 is preferably directed to steam generator 122 to produce steam product 124 and exiting process stream 125. Exiting process stream 125 may be returned directly to reactor via optional line 126 and return line 127. Reaction solution stream 121 comprises the components of the reaction medium and preferably is retained with the system and not purged. After passing through steam generators, exiting process stream 125 may have a temperature below the carbonylation reaction temperature, e.g., below about 205° C., or from 150° C. to 185° C. In preferred embodiments, each pump around loop produces at least 5 tns/hr of steam, e.g., at least 15 tns/hr, 20 tns/hr or 25 tns/hr. In terms of ranges each around loop may produce from 5 to 30 tns/hr, e.g., from 5 to 25 tns/hr or 5 to 20 tns/hr. In addition, in preferred embodiments, the steam produced may have variable qualities (pressure). The pressure may be at least 4 bars, e.g., at least 5 bars, or at least 6 bars. The quantity of steam produced by the steam generators from the heat transfer system 120 may vary based on the flow rate, control temperature in the carbonylation system reactor, condensate temperature, and the pressure quality of the steam being generated. Certain embodiments of the present invention enable the generation of high quantity, variable quality (i.e., pressure) steam to supply up to 100%, e.g., up to 80% or up to 50%, of steady state steam demand for the purification sections of the carbonylation system process.

In addition, steam product 124 may be used to drive other systems in the carbonylation process such as turbine driven pumps, to flare, to heat storage tanks and/or buildings, to absorption refrigeration systems, etc. Also steam product 124 may be used in other chemical units, such as, for example, anhydride production units and/or ester units. In some embodiments, steam product 124 is directed to an external energy consuming process. For example, steam product 124 can be directed to an acetic anhydride production process, a vinyl acetate production process, and combinations thereof. Non-limiting examples of acetic anhydride production processes are described in U.S. Pat. Nos. 7,199,263 and 4,544,511, the disclosures of which are incorporated by reference herein in their entirety. Non-limiting examples of vinyl acetate production processes are described in U.S. Pat. Nos. 3,190,912, 3,637,819, 4,370,492, 4,902,823, 5,185,308 and 7,465,823, the disclosures of which are incorporated herein by reference in their entirety.

Suitable steam generators may include a shell and tube exchanger, double pipe exchanger, spiral plate exchanger, plate heat exchanger, helical coil, spiral coil or bayonet tube in tank heat exchanger, or any other suitable heat exchanger known in the art. The process side of the steam generator can be comprised of any suitable material known in the art, for example a nickel-molybdenum alloy such as HASTELLOY™ B-3 alloy (Haynes International) or a zirconium alloy such as Zirc™ 702 alloy (United Titanium Inc.). The steam (water) side of the steam generator can be comprised of any suitable metal, including carbon steel and lower grade stainless and alloy steels.

In one embodiment, reactor solution stream 121 may be directed to heat exchanger 123 to provide temperature regulation of reactor 105, via optional line 128. The outflow of heat exchanger 123 may be returned to reactor via return line 127. Any suitable indirect-contact heat exchangers, including two medium transfer type heat exchangers or three medium transfer type heat exchangers, that are capable of transferring heat by conduction may be used with embodiments of the present invention. Heat exchangers may include a shell and tube exchanger, spiral plate heat exchanger, helical coil exchanger, or any other suitable heat exchanger known in the art. Sensible cooling heat exchangers are preferred. These heat exchangers preferably provide bulk and/or trim cooling to remove the excess heat of the reaction from the carbonylation reaction of the system. In addition, in some embodiments, heat exchangers and may also produce steam. In still other embodiments, heat exchangers are used to provide heat to reactor 105 during start up and steam generator 122 may be bypassed by optional line 128. After passing through one of the heat exchangers in cooling mode, the outflow may have a temperature below the carbonylation reaction temperature, e.g., below about 175° C., or from 30° C. to 175° C.

In addition, in some embodiments, steam generator may also provide temperature regulation of the carbonylation reactor with or without producing steam. Steam generator and heat exchanger may be used in combination to provide temperature regulation. For example, when reactor is cooled about a third of the cooling may be provided by the steam generator and the remaining cooling provided by the heat exchanger.

In a preferred embodiment, reactor solution stream 121 is fed to steam generator 122 and a portion of exiting process stream 125 is directed to heat exchanger 123 to provide trim cooling of the reactor 105. The outflow of heat exchanger 123 may be returned to reactor 105 via line 127. Preferably reaction solution stream 121 is withdrawn and return line 127 fed to reactor below the liquid level in reactor 105. In some embodiments, reaction solution stream 121 is withdrawn below the level at which carbonylation product 114 is withdrawn from the reactor 105. In one embodiment, reaction solution stream 121 and return line 127 may be connected to reactor 105 at similar elevations but at differing orientations.

Returning to crude product stream 115, a purification section 102 preferably controls water and acetic acid content in reactor 105, as well as throughout the system and, optionally, controls the removal of permanganate reducing compounds (PRC's). PRC's may include, for example, compounds such as acetaldehyde, acetone, methyl ethyl ketone, butyraldehyde, crotonaldehyde, 2-ethyl crotonaldehyde, 2-ethyl butyraldehyde and the like, and the aldol condensation products thereof.

The exemplary carbonylation system depicted herein may also include further systems and components that may be used with embodiments of the present invention include those described in U.S. Pat. Nos. 7,223,886, 7,005,541, 6,6657, 078, 6,339,171, 5,731,252, 5,144,068, 5,026,908, 5,001,259, 4,994,608, and U.S. Pub. Nos. 2008/0287706, 2008/0293966, 2009/0107833, 2009/0270651, the entire contents and disclosures of which are hereby incorporated by reference. It should be understood that the carbonylation system shown in the figures is exemplary and other components may be used with the scope of the present invention.

Figure 2:
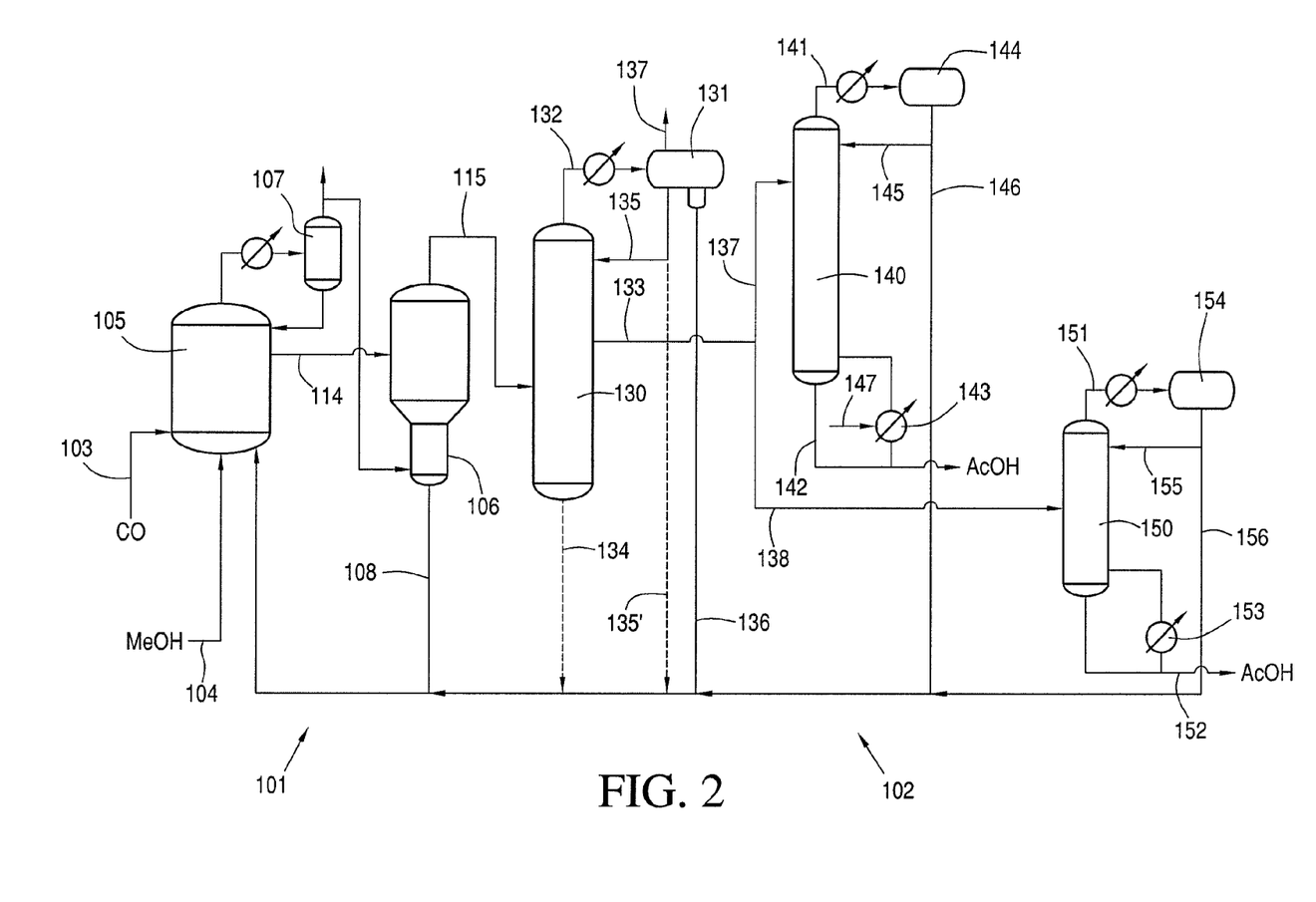
FIG. 2 illustrates a carbonylation system having multiple drying columns according to an embodiment of the present invention.

Referring to FIG. 2, reaction section 101 comprises carbon monoxide feed stream 103, reactant feed stream 104, reactor 105, flasher 106, and reactor vent recovery unit 107 as described above in FIG. 1. Crude product stream 115 is directed to a purification section 102 comprising a light ends column 130, an overhead decanter 131, a first drying column 140, and a second drying column 150. Purification sections suitable for embodiments of the present invention may also comprise one or more columns for removal of PRC's, guard beds, vent scrubbers/absorbers, and/or heavy ends columns (not shown). The PRC removal columns are described in U.S. Pat. Nos. 6,143,930, 6,339,171, and 7,223,886, and U.S. Pub. Nos. 2005/0197513, 2006/0247466, and 2006/0293537, the entire contents and disclosures of which are hereby incorporated by reference. Guard beds are described in U.S. Pat. Nos. 4,615,806, 4,894,477, and 6,225,498, the entire contents and disclosures of which are hereby incorporated by reference.

In one embodiment, crude product stream 115 from reaction section 101 is fed to light ends column 130 to obtain a low-boiling overhead vapor stream 132, a product side stream 133, and an optional bottoms stream 134. The temperature at the base of the light ends column 130, i.e., temperature of the optional exiting bottoms stream 134, preferably is from 120° C. to 170° C. In addition, the temperature at the top of the light ends column, i.e., temperature of low-boiling overhead vapor stream 132, preferably is from 100° C. to 145° C.

Low-boiling overhead vapor stream 132 may comprise methyl iodide, methyl acetate, water, PRC's, acetic acid, alkanes, and dissolved gases. As shown, low-boiling overhead vapor stream 132 preferably is condensed and directed to an overhead phase separation unit, as shown by overhead decanter 131. Conditions are desirably maintained such that low-boiling overhead vapor stream 132, once in decanter 131, will separate into a light phase 135 and a heavy phase 136. Non-condensable gases may be removed by vent stream 137 and optionally fed to one or more scrubbers (not shown) to recover any low boiling point components.

The light phase 135 preferably comprises water, acetic acid, and PRC's, as well as methyl iodide and methyl acetate. As shown in FIG. 2, light phase 135 may be refluxed to light ends column 130. A portion of the light phase 135 may also be separated and processed in one or more columns (not shown) to remove PRC's. Optionally, a portion of the light phase 135 may also be returned to reaction section 101 via stream 135' and co-fed with recycle stream 108 to reactor 105. The heavy phase 136 from the decanter 131 can be conveniently recirculated, either directly or indirectly, to the reactor 105 via recycle stream 108. For example, a portion of the heavy phase 136 may be recirculated to the reactor 105, with a slip stream (not shown), generally a small amount, e.g., from 5 to 40 vol. %, or from 5 to 20 vol. %, of the heavy phase 136 being directed to the one or more columns to remove PRC's (not shown).

Product side stream 133 from the light ends column may comprise acetic acid and water. Product side stream 133 preferably is in the liquid phase and is withdrawn from the light ends column 130 at a temperature from 115° C. to 160° C., e.g., from 125° C. to 155° C.

Under steady state operating conditions the amount of product side stream that may be fed to a drying column may be limited. One potential limitation may be the capacity of the drying column to remove water from a product side stream. Thus, although the amount of product side stream fed to the drying column may be increased, it may be difficult to remove a sufficient amount of water from the product side stream. As the product side stream is fed to drying column there may be a hold up of liquid at a hat tray Embodiments of the present invention may increase the capacity of the drying process by drying a first portion of a product side stream in a first drying column and drying a second portion of the product side stream in a second drying column. In some embodiments, the second drying column operates independently of the first drying column, i.e., the second drying column operates at a lower base temperature and lower base pressure than the first drying column. While not being bound to one particular theory, operating the second drying column at a lower base temperature and lower base pressure reduces the steam pressure quality required to drive separation in the second drying column.

Product side stream 133 may be divided into two or more streams and each stream may be fed to a separate drying column. In one embodiment, a first portion of product side stream 133 may be fed to a first drying column 140 via line 137. A second portion of product side stream 133 may be fed to a second drying column 150 via line 138. In one embodiment, the first portion may be larger than the second portion.

First drying column 140 separates an overhead stream 141 comprised primarily of water and a first dried product stream 142. The first dried purified product stream 142 preferably comprises acetic acid in an amount greater than 90 wt. %, e.g., greater than 95 wt. % or greater than 98 wt. %. Optionally, the dried purified product stream 142 may be further treated in one or more guard beds (not shown) and/or heavy end columns (not shown) to further remove impurities. Overhead stream 141 of the first drying column may be condensed and separated in a receiver 144. A portion of the liquid from receiver 144 may be refluxed to drying column 140 via line 145 and another portion may be returned to the reaction section 101 via line 146 and co-fed with recycle stream 108 to reactor 105. In some embodiments, the temperature at the base of first drying column 140, i.e., temperature of the exiting dried purified product stream 142, preferably is from 130° C. to 185° C., 140° C. to 180° C., e.g., from 150° C. to 175° C.

In some embodiments, the temperature at the top of first drying column 140, i.e., temperature of the overhead stream 141, preferably is from 110° C. to 150° C., 120° C. to 150° C., e.g., from 130° C. to 145° C. In some embodiments, the pressure in first drying column 140 is from 2 bar(a) to 7 bar(a), e.g., 3 bar(a) to 6 bar(a), or 4 bar(a) to 5 bar(a).

In some embodiments, a portion of the first dried product stream 142 may be fed to a reboiler 143 attached to the first drying column 140. Reboiler 143 heats stream 142 and a mixed liquid/vapor stream to the first drying column 140, wherein the vapor provides a portion of the energy to drive separation in the first drying column. A portion of the energy required to drive reboiler 143 is provided by external steam via line 147.

A second portion of product side stream 133 may be fed to a second drying column 150 via stream 138 to obtain an overhead stream 151 comprised primarily of water and a second dried product stream 152. The second dried purified product stream 152 preferably comprises acetic acid in an amount greater than 90 wt. %, e.g., greater than 95 wt. % or greater than 98 wt. %. Optionally, the dried purified product stream 152 may be further treated in one or more guard beds (not shown) and/or heavy end columns (not shown) to further remove impurities. Dried purified product stream 152 may be used when off-spec product is produced from second column 150. In one embodiment, dried purified product stream 142 and dried purified product stream 152 may be combined and treated in a common guard bed. Overhead stream 151 of the second drying column may be condensed and separated in a receiver 154. A portion of the liquid from receiver 154 may be refluxed to drying column 150 via line 155 and another portion may be returned to reaction section 101 via line 156 and co-fed with recycle stream 108 to reactor 105.

In some embodiments, the temperature at the base of the second drying column is less than the temperature at the base of the first drying column. Preferably, the temperature at the base of second drying column 150, i.e., temperature of the exiting dried purified product stream 152, preferably is from 125° C. to 175° C., 140° C. to 170° C., e.g., 155° C. to 165° C. In some embodiments, the temperature at the top of the second drying column is lower than the temperature at the top of the first drying column. Preferably, the temperature at the top of the second drying column 150, i.e., temperature of the overhead stream 151, preferably is from 100° C. to 140° C., 120° C. to 150° C., e.g., 125° C. to 135° C. In some embodiments, the pressure of the second drying column is less than the pressure at the base of the first drying column. In some embodiments, the pressure at the base of the second drying column 150 is from 1 bar(a) to 5 bar(a), e.g., 2 bar(a) to 4 bar(a), or 3 bar(a) to 3.5 bar(a).

In some embodiments, a portion of the second dried product stream 152 may be fed to a reboiler 153 attached to the second drying column 150. Reboiler 153 heats stream 152 and recycles a mixed liquid/vapor stream to the second drying column 150, wherein the vapor provides a portion of the energy required to drive separation in the second drying column.

During the production of acetic acid, the process preferably operates continuously under normal steady state conditions. However, due to start up, reactor shutdown, reactor rate reductions, trips, or distillation train upsets, the production distillation process may operate under partial conditions. When operating under these partial conditions and outside of normal operation, the amount of product side stream 133 fed via line 137 to the first drying column 140 and/or via line 138 to the second drying column 150 can be adjusted to increase the efficiency of the process. For example, during normal operation, a majority of the product side stream 133 is fed to the first drying column 140, preferably greater than 50 wt. %, e.g., greater than 60%, or greater than 66%, of the product side stream 133 may be fed to the first drying column 140. The remaining portion, under normal operating conditions, may be fed to second drying column, e.g., less than 50 wt. %, less than 40 wt. %, or less than 33 wt. %.

Under some circumstances the portion directed to second drying column 150 may be larger than the first drying column 140. During partial operation, a majority of the product side stream 133 may be fed to second drying column 150, preferably greater than 50 wt. %, e.g. greater than 70 wt. %, greater than 80 wt. % or greater than 90 wt. %, of the product side stream 133 is fed to the second drying column 150. In some embodiments, such as during reactor shutdown operation, a majority of the product side stream 133 may be fed to the second drying column 150, preferably greater than 50 wt. %, e.g. greater than 70 wt. %, greater than 80 wt. % or greater than 90 wt. %, of the product side stream 133 is fed to the second drying column 150. Also, during reactor or purification start up, a majority of the product side stream 133 is initially fed to the second drying column 150, preferably greater than 50 wt. %, e.g. greater than 70 wt. %, greater than 80 wt. % or greater than 90 wt. %, of the product side stream 133 is fed to the second drying column 150. In one embodiment, during any of these circumstances, the first drying column may be shut down and the second drying column may receive the entire product side stream.

Embodiments of the present invention increase the efficiency of the carbonylation process through heat integration within the system. For example, in some embodiments, steam is generated by the removal of heat from the reaction, and the steam provides a portion of the energy required to drive separation in the purification section. In particular the steam may used to drive separation in a secondary drying column as shown in FIG. 3.

Figure 3:
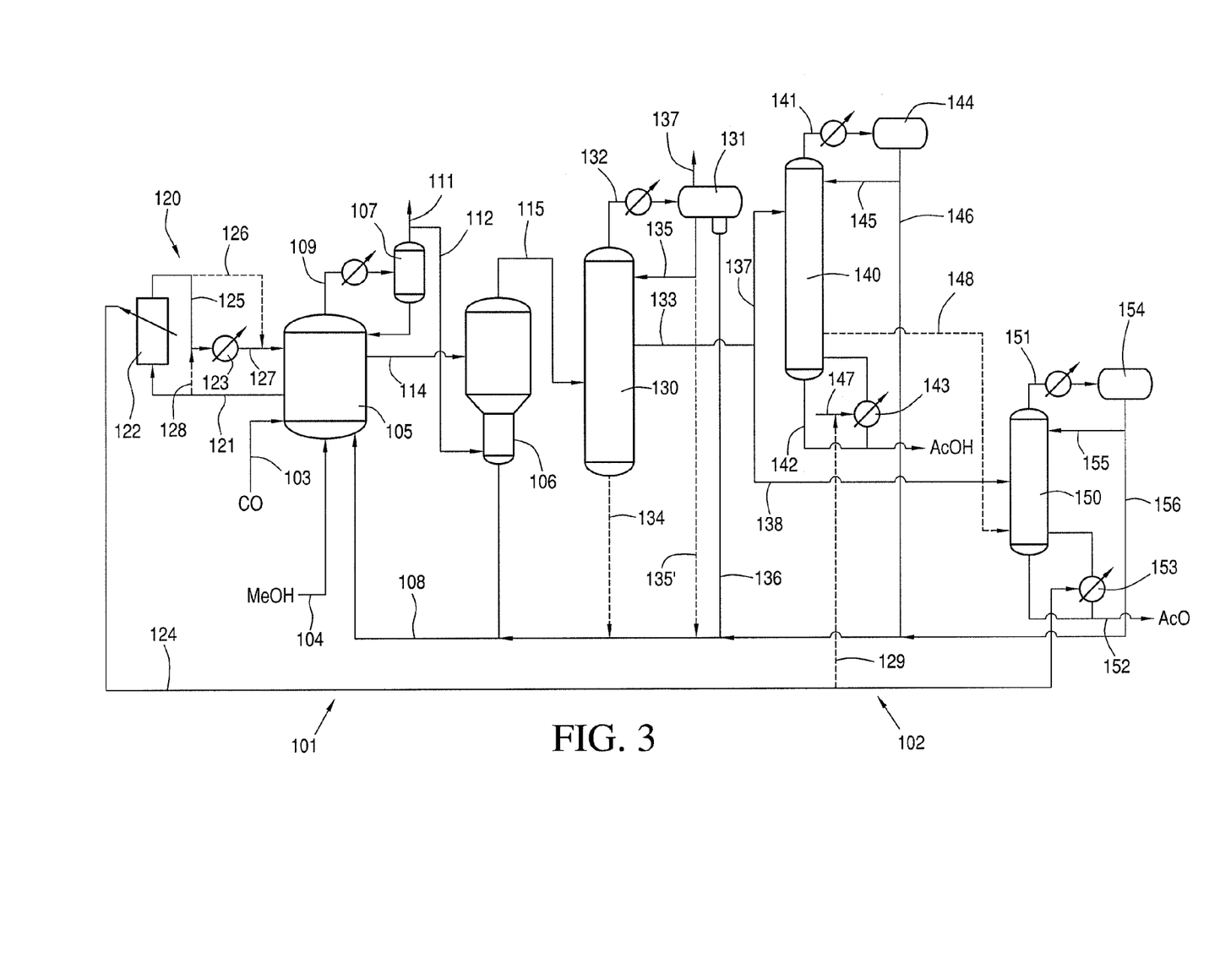
FIG. 3 illustrates a carbonylation system having multiple drying columns and internal heat integration according to an embodiment of the present invention.

As shown in FIG. 3, steam product 124 produced in heat transfer system 120 may be directed to reboiler 153 of second drying column 150. Steam product 124 may supply all or a portion of the energy required to drive second drying column 150. The integration of steam product 124 and second drying column 150 provides an efficiency increase of production capacity by using the additional heat from the reactor to separate the acetic acid product.

In some embodiments, steam product 124 may also be directed to another portion of the purification section 102. As indicated by line 129, a portion of steam product 124 may be used to drive first drying column 140 through integration with reboiler 143. In some embodiments, steam product 124 provides a portion of the energy required to drive separation in the first drying column 140 and the second drying column 150. In some embodiments, steam product 124 provides a portion of the energy required to drive reboiler 143 and reboiler 153.

Optionally, one or more vapor streams 148 are drawn from the first drying column 140 and fed to the second drying column 150. Vapor streams 148 are drawn from the stripping section of the first drying column 140 and are fed to a lower portion of the second drying column 150, preferably above the liquid level in the base of the second drying column. While not being bound to one particular theory, optionally feeding one or more vapor streams 148 from first drying column 140 to second drying column 150 may allow using the larger capacity of the reboilers 143 of the first drying column 140 to handle a net higher throughput of purified product stream 133, using stream 124 as the energy source.

One of ordinary skill in the art having the benefit of this disclosure can design and operate the distillation columns described herein to achieve the desired results of the present invention. Such efforts, although possibly time-consuming and complex, would nevertheless be routine for one of ordinary skill in the art having the benefit of this disclosure. Accordingly, the practice of this invention is not necessarily limited to specific characteristic of a particular distillation column or the operation characteristics thereof, such as the total number of stages, the feed point, reflux ratio, feed temperature, reflux temperature, column temperature profile, and the like.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

I claim:

1. A carbonylation method of producing acetic acid comprising the steps of:

reacting carbon monoxide with at least one reactant in a reactor containing a reaction medium to produce a reaction product comprising acetic acid, wherein the at least one reactant is selected from the group consisting of methanol, methyl acetate, methyl formate, dimethyl ether and mixtures thereof, and wherein the reaction medium comprises water, a halogen promoter, and a catalyst, separating the reaction product in a flasher to produce a crude product stream and a liquid recycle stream;

purifying the crude product stream in a light ends column to produce a purified product stream;

drying a first portion of the purified product stream in a first drying column; and drying a second portion of the purified product stream in a second drying column.

2. The method according to claim 1, further comprising:

generating steam from heat from the reaction that produces the reaction product in a heat transfer system; and transferring at least a portion of the steam to the second drying column, wherein the steam provides a portion of the energy required to drive separation in the second drying column.

3. The method according to claim 2, wherein the at least a portion of the steam is transferred to a reboiler of the second drying column.

4. The method according to claim 2, wherein the heat transfer system further comprises one or more heat exchangers.

5. The method according to claim 1, further comprising transferring one or more vapor streams from the first drying column to the second drying column.

6. The method according to claim 1, wherein the second drying column has a base temperature lower than a base temperature of the first drying column.

7. The method according to claim 6, wherein the base temperature of the second drying column is from 125° C. to 175° C.

8. The method according to claim 1, wherein the second drying column has a pressure lower than a pressure of the first drying column.

9. The method according to claim 8, wherein the pressure of the second drying column is from 1 bar(a) to 5 bar(a).

10. The method according to claim 1, wherein the reactor operates at an elevated reaction temperature from about 190° C. to about 225° C.

11. A method for controlling the reaction temperature in an acetic acid production process comprising the steps of:

reacting carbon monoxide with at least one reactant in a reactor containing a reaction medium to produce a reaction product comprising acetic acid, wherein the at least one reactant is selected from the group consisting of methanol, methyl acetate, methyl formate, dimethyl ether and mixtures thereof, and wherein the reaction medium comprises water, a halogen promoter, and a catalyst, separating the reaction product in a flasher to produce a crude product stream and a liquid recycle stream;

distilling the crude product stream to produce an acetic acid product stream in one or more distillation columns, wherein the one or more distillation columns comprises a first drying column and a second drying column; and generating steam from heat of the reaction that produces the reaction product in a heat transfer system.

12. The method of claim 11, further comprising transferring a portion of the steam to the one or more distillation columns, wherein the steam provides a portion of the energy required to drive separation in the one or more distillation columns.

13. The method of claim 11, wherein a portion of the steam is transferred to a reboiler of the second drying column.

14. The method of claim 11, wherein a portion of the steam is transferred to a reboiler of the first drying column.

15. The method according to claim 11, wherein the second drying column has a base temperature lower than a base temperature of the first drying column.

16. The method according to claim 15, wherein the base temperature of the second drying column is from 125° C. to 175° C.

17. The method according to claim 11, wherein the second drying column has a pressure lower than a pressure of the first drying column.

18. The method according to claim 17, wherein the pressure of the second drying column is from 1 bar(a) to 5 bar(a).

19. The method according to claim 11, wherein the reactor operates at an elevated reaction temperature from about 190° C. to about 225° C.

\* \* \* \* \*